United States Patent
Wei et al.

(10) Patent No.: US 9,403,735 B2
(45) Date of Patent: Aug. 2, 2016

(54) FLUIDIZED BED REACTOR AND PROCESS FOR PRODUCING OLEFINS FROM OXYGENATES

(75) Inventors: Fei Wei, Beijing (CN); Xiaobo Wei, Beijing (CN); Yao Wang, Beijing (CN); Chang Zhu, Beijing (CN)

(73) Assignees: FUDE (BEIJING) CHEMICAL & INDUSTRY CO., LTD, Beijing (CN); TSINGHUA UNIVERSITY, Beijing (CN)

(*) Notice: Subject to any disclaimer, the term of this patent is extended or adjusted under 35 U.S.C. 154(b) by 234 days.

(21) Appl. No.: 14/124,502

(22) PCT Filed: May 30, 2012

(86) PCT No.: PCT/CN2012/076249
§ 371 (c)(1),
(2), (4) Date: Dec. 6, 2013

(87) PCT Pub. No.: WO2012/167708
PCT Pub. Date: Dec. 13, 2012

(65) Prior Publication Data
US 2014/0121434 A1  May 1, 2014

(30) Foreign Application Priority Data
Jun. 8, 2011 (CN) .......................... 2011 1 0150648

(51) Int. Cl.
*C07C 1/00* (2006.01)
*C07C 1/20* (2006.01)
(Continued)

(52) U.S. Cl.
CPC ................ *C07C 1/22* (2013.01); *B01J 8/0055* (2013.01); *B01J 8/1836* (2013.01); *B01J 8/1863* (2013.01);
(Continued)

(58) Field of Classification Search
CPC ............. C07C 1/00; C07C 1/20; C07C 1/22; C07C 2529/82; C07C 2529/84; C07C 2529/85; Y02P 20/50; Y02P 20/58; Y02P 20/584; B01J 8/00; B01J 8/005; B01J 8/0055; B01J 8/18; B01J 8/01836; B01J 8/1845; B01J 8/1863; B01J 8/24; B01J 8/26; B01J 8/28; B01J 19/00; B01J 19/24
See application file for complete search history.

(56) References Cited

U.S. PATENT DOCUMENTS 3,970,587 A * 7/1976 Shinnar ...................... B01J 8/26
208/120.01
4,547,616 A 10/1985 Avidan et al.
(Continued)

FOREIGN PATENT DOCUMENTS

CN            1166478        12/1997
CN           101164684        4/2008
(Continued)

OTHER PUBLICATIONS

Extended search Report issued Nov. 19, 2015 in European Patent Application No. 12797214.9.
(Continued)

*Primary Examiner* — Natasha Young
(74) *Attorney, Agent, or Firm* — Oblon, McClelland, Maier & Neustadt, L.L.P

(57) ABSTRACT

The present invention provides a fluidized bed reactor and its use for producing olefins from oxygenates, the fluidized bed reactor comprises: a reaction zone located in the lower portion of the fluidized bed reactor and comprising a lower dense phase zone and an upper riser, wherein the dense phase zone and the riser are connected with each other transitionally; a separation zone located in the upper portion of the fluidized bed reactor and comprising a settling chamber, a fast gas-solid separation means, a cyclone and a gas collecting chamber, wherein the riser extends upwardly into the separation zone and is connected at its outlet with the inlet of the fast gas-solid separation means, the fast gas-solid separation means is connected at its outlet with the inlet of the cyclone via a fast gas passage, the cyclone is connected at its outlet with the gas collecting chamber, and the gas collecting chamber is located below the reactor outlet and connected therewith; and a catalyst recycle line for recycling the catalyst from the settling chamber back to the dense phase zone, a catalyst withdrawl line for withdrawing the deactivated catalyst from the settling chamber and/or the dense phase zone to the catalyst regeneration means, and a catalyst return line for returning the regenerated catalyst from the catalyst regeneration means to the dense phase zone.

20 Claims, 1 Drawing Sheet

(51) Int. Cl.
*C07C 1/22* (2006.01)
*B01J 8/00* (2006.01)
*B01J 8/18* (2006.01)
*B01J 8/24* (2006.01)
*B01J 8/26* (2006.01)
*B01J 8/28* (2006.01)
B01J 19/00 (2006.01)
B01J 19/24 (2006.01)

(52) U.S. Cl.
CPC .... *B01J 8/24* (2013.01); *B01J 8/28* (2013.01); *C07C 1/20* (2013.01); *C07C 2529/85* (2013.01); *Y02P 20/584* (2015.11)

(56) References Cited

U.S. PATENT DOCUMENTS

| | | | |
|---|---|---|---|
| 4,895,636 A * | 1/1990 | Chen | C10G 11/18 208/113 |
| 5,183,558 A * | 2/1993 | Owen | C10G 11/182 208/113 |
| 6,023,005 A | 2/2000 | Lattner et al. | |
| 6,166,282 A | 12/2000 | Miller | |
| 7,169,293 B2 | 1/2007 | Lomas et al. | |
| 7,575,725 B2 | 8/2009 | Lomas et al. | |
| 2004/0104148 A1 | 6/2004 | Lomas et al. | |
| 2004/0104149 A1 | 6/2004 | Lomas et al. | |
| 2007/0122316 A1 | 5/2007 | Lomas et al. | |
| 2009/0117017 A1 * | 5/2009 | Long | B01J 8/0055 422/600 |
| 2009/0163756 A1 | 6/2009 | Pujado | |
| 2010/0028224 A1 * | 2/2010 | Miller | B01J 8/0055 422/212 |
| 2010/0063335 A1 | 3/2010 | Xie et al. | |
| 2011/0240523 A1 * | 10/2011 | Mandal | C10G 11/18 208/120.01 |

FOREIGN PATENT DOCUMENTS

| | | |
|---|---|---|
| CN | 101164685 | 4/2008 |
| CN | 101439278 | 5/2009 |
| EP | 2 070 592 A2 | 6/2009 |
| EP | 2 070 592 A3 | 6/2009 |
| WO | WO 02/085527 A2 | 10/2002 |
| WO | WO 02/085527 A3 | 10/2002 |

OTHER PUBLICATIONS

Office Action issued Feb. 24, 2015 in Canadian Patent Application No. 2,859,723.
Office Action issued Feb. 26, 2015 in Australian Patent Application No. 2012267002.
Office Action issued Mar. 19, 2015 in Russian Patent Application No. 2013157347 (with English language translation).
International Search Report Issued Sep. 27, 2012 in PCT/CN12/076249 Filed May 30, 2012.
Chinese Office Action Issued Jul. 1, 2013 in CN Application No. 2011101506483.3 Filed Jun. 8, 2011.

* cited by examiner

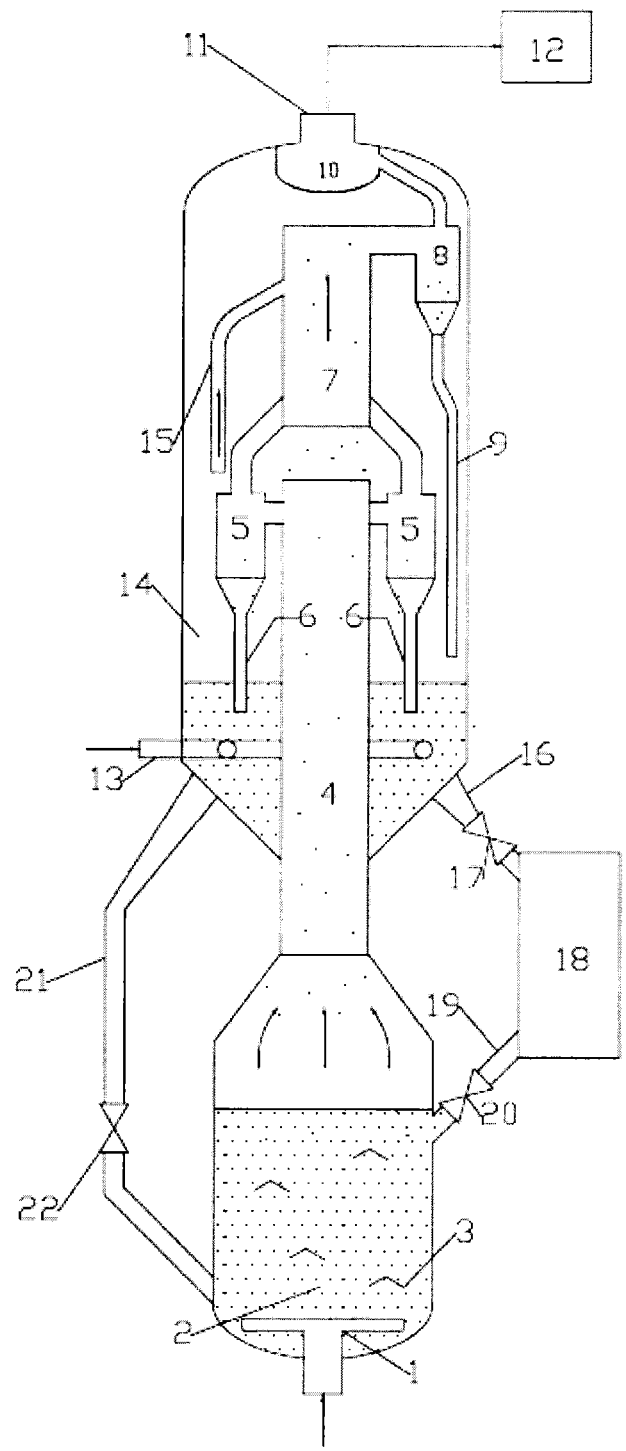
The fluidized bed reactor according to the present invention

FLUIDIZED BED REACTOR AND PROCESS FOR PRODUCING OLEFINS FROM OXYGENATES

TECHNICAL FIELD

The present invention relates to a fluidized bed reactor for producing olefins from oxygenates as well as a process for producing olefins from oxygenates using said fluidized bed reactor.

TECHNICAL BACKGROUND

It is known that aluminosilicophosphate (SAPO) molecular sieves can be used as the catalyst for converting lower carbon oxygenates such as methanol and/or dimethyl ether to lower olefins such as ethylene, propylene and butylene. Hereinto, a series of SAPO molecular sieves such as SAPO-5, SAPO-11, SAPO-17, SAPO-41, SAPO-34 and SAPO-41 have been developed as catalysts, e.g. for converting oxygenates to olefins, and it is well known that SAPO-34, when being used for producing olefins from methanol and/or dimethyl ether (MTO), has excellent catalytic properties due to small pore diameter and good hydrothermal stability.

Producing olefins from oxygenates is effected primarily by catalytic cracking, which is generally an exothermic process. Specifically, as to producing lower olefins such as ethylene, propylene and etc. from methanol and/or dimethyl ether, the targeted product is ethylene and propylene, however, during the process butylene, pentene, hexene as well as their corresponding alkanes are produced at minor amounts too, this is because during the process, in addition to that methanol and/or dimethyl ether being catalytically cracked to olefins, the produced olefins may further subject to secondary reactions such as conversions between each other, e.g. ethylene and/or propylene may further oligomerize to $C_{4+}$ olefins.

Thus, in order to increase the production of ethylene and propylene, not only the overall conversion of the process has to be improved to convert the reactants as much as possible, but also the overall selectivity to ethylene and/or propylene has to be improved too. Thus, for certain SAPO catalysts, the reactants have to contact with the catalyst sufficiently to get converted as much as possible, however, the product gases have to contact with the catalyst as little as possible to avoid or minimize secondary reactions such as the oligomerizations of ethylene and/or propylene to higher olefins.

Regarding the reactions for producing olefins from oxygenates such as MTO, there are some reactors being developed in the prior art, including dense phase fluidized bed reactor and riser. For example, CN1166478A disclosed a process for producing lower olefins such as ethylene, propylene and etc. from methanol or dimethyl ether, wherein SAPO-34 molecular sieve is used as the catalyst to carry out reaction and gets regenerated continuously in a dense phase circulation fluidized bed reactor; U.S. Pat. No. 4,547,616 disclosed a continuous process for producing lower olefins from oxygenates using a turbulent fluidized bed, wherein the turbulent fluidized bed is also a dense phase fluidized bed reactor; and U.S. Pat. No. 6,023,005 disclosed a process for converting oxygenates to olefins in the presence of molecular sieves as catalyst, wherein a riser is used as the reactor.

As to the dense phase fluidized bed reactor, a heat removing means may be incorporated into the bed so that the reaction temperature can be controlled easily, however, due to a serious gas and solid backmixing in the dense phase zone, a big catalyst inventory is necessary to ensure the conversion of the feed and at the same time a bigger settling chamber is necessary to separate the catalyst from the product gases, thus, there is a great chance for the secondary reactions, which is not favorable to the overall selectivity to ethylene and propylene during the process.

As to the riser, due to the gas and solid traveling upwardly co-currently with less backmixing, the catalyst inventory may be reduced, however, it is not easy to control the reaction temperature in the riser; furthermore, due to the slower reaction velocity from oxygenates to olefins, it is hardly to convert the feed completely by riser reactor.

U.S. Pat. No. 6,166,282 disclosed a fast fluidized bed reactor for MTO process, which comprises an upper separation zone and a lower reaction zone, wherein the reaction zone comprises a dense phase zone and a transition zone above the dense phase zone, and the reactants are further converted completely after being reacted in the dense phase zone. Compared with the conventional bubbling bed, the fast fluidized bed significantly reduces the reactor size and the catalyst inventory and thus saves the cost, however, the gas and solid backmixing problem is still present and the gas entering into the settling chamber needs more time to enter into the cyclone, thus, this gas may still subject to secondary reactions, which is not favorable to the overall selectivity to ethylene and propylene.

Thus, some further improvements are still needed for the reactor and process for producing olefins from oxygenates, in order to improve the conversion of the reactants as well as the selectivity to the products.

SUMMARY OF THE INVENTION

Viewing the situation of the prior art, the present invention provides a fluidized bed reactor for producing olefins from oxygenates and a process for producing olefins from oxygenates using the fluidized bed reactor.

In one aspect, the present invention provides a fluidized bed reactor for producing olefins from oxygenates, which fluidized bed reactor comprises:

A reaction zone located in the lower portion of the fluidized bed reactor and comprising a lower dense phase zone and an upper riser, wherein the dense phase zone and the riser are connected with each other transitionally;

A separation zone located in the upper portion of the fluidized bed reactor and comprising a settling chamber, a fast gas-solid separation means, a cyclone and a gas collecting chamber, wherein the riser extends upwardly into the separation zone and is connected at its outlet with the inlet of the fast gas-solid separation means, the fast gas-solid separation means is connected at its outlet with the inlet of the cyclone via a fast gas passage, the cyclone is connected at its outlet with the gas collecting chamber, and the gas collecting chamber is located below the reactor outlet and connected therewith; and A catalyst recycle line for recycling the catalyst from the settling chamber back to the dense phase zone, a catalyst withdrawal line for withdrawing the deactivated catalyst from the settling chamber and/or the dense phase zone to the catalyst regeneration means, and a catalyst return line for returning the regenerated catalyst from the catalyst regeneration means to the dense phase zone.

In another aspect, the present invention further provides a process for producing olefins from oxygenates using the fluidized bed reactor as above described and comprising the steps of:

Introducing a feed stream comprising oxygenates and a diluent into the dense phase zone in the lower portion of the fluidized bed reactor via the feed inlet distributor, wherein the feed stream is reacted in the presence of a catalyst so that a part of the feed is converted to lower olefins and a part of the catalyst gets deactivated due to carbon deposition thereon;

Directing a reaction mixture comprising lower olefins, unreacted feed and catalyst from the dense phase zone upwardly into the riser, wherein the unreacted feed is further converted almost completely in the presence of the catalyst, thus yielding a riser effluent primarily comprising lower olefins and catalyst;

The riser effluent is entering directly into the separation zone in the upper portion of the fluidized bed reactor, firstly into the fast gas-solid separation means wherein most of the catalyst is separated, then via the fast gas passage into the cyclone wherein the remaining catalyst is separated furthermore, then into the gas collecting chamber, and then exiting through the reactor outlet, and all the separated catalyst falls into the settling chamber in the lower portion of the separation zone; and A part of the catalyst is recycled from the settling chamber back to the dense phase zone via the catalyst recycle line, a part of the deactivated catalyst is withdrawn via the catalyst withdrawal line from the settling chamber and/or the dense phase zone to the catalyst regeneration means to be regenerated therein, and then a part of the regenerated catalyst is returned from the catalyst regeneration means to the dense phase zone via the catalyst return line.

According to the present invention, the dense phase zone in the fluidized bed reactor may further comprise internals for removing reaction heat and/or inhibiting gas and solid backmixing, e.g. the internals may be heat exchanging internals such as heat exchanger or heat exchanging coil, or may be backmixing-inhibiting internals such as flow-guiding plates or baffles, or even may be combinations of these internals for being simplified and highly efficient in some cases, so that to control the reaction temperature better and/or reach a higher conversion of feed.

According to the present invention, the fluidized bed reactor is designed in such a size that the dense phase zone has a height to diameter ratio in the range of 0.5-10, preferably in the range of 0.6-8, more preferably in the range of 0.8-5, the riser has a height to diameter ratio in the range of 2-20, preferably in the range of 3-15, more preferably in the range of 4-10, and the diameter ratio between the dense phase zone and the riser is in the range of 2-10, preferably in the range of 2.5-8, more preferably in the range of 3-6; and during the process for producing olefins from oxygenates using the fluidized bed reactor, said fluidized bed reactor is operated in such a way that when passing the dense phase zone, the stream has a superficial gas velocity in the range of 0.1-2 m/s, preferably in the range of 0.2-1.5 m/s, more preferably in the range of 0.3-1.2 m/s, and a residence time in the range of 0.5-20 s, preferably in the range of 1-15 s, more preferably in the range of 2-10 s, and when passing the riser, the stream has a superficial gas velocity in the range of 2-20 m/s, preferably in the range of 4-18 m/s, more preferably in the range of 5-15 m/s, and a residence time in the range of 0.3-5 s, preferably in the range of 0.4-4 s, more preferably in the range of 0.5-3 s, thus, the feed load can be distributed reasonably within the reaction zone to reach the targeted conversion.

According to the present invention, in the fluidized bed reactor, the settling chamber is located in the lower portion of the separation zone to collect the catalyst separated in the separation zone, and the settling chamber may comprise: a stripping gas distributor at its inside to introduce a stripping gas to strip the catalyst, herein the stripping gas may be nitrogen or steam, preferably steam, thus the feed gas and/or product gas entrained by the catalyst may be further separated by the stripping operation, and a stripped mixture guiding line at its upper side for passing the stripped mixture to the cyclone to be separated.

According to the present invention, in the fluidized bed reactor, the fast gas-solid separation means may be any fast gas-solid separation means known to be suitable in the art, e.g. the fast gas-solid separation means may be selected from the group consisting of a vortex type fast gas-solid separation means, an ejection type fast gas-solid separation means, an inverse L type fast gas-solid separation means, a T type fast gas-solid separation means, a multi-lobe type fast gas-solid separation means and a rotary arm type fast gas-solid separation means, thus, the gas phase and the solid phase in the riser effluent can be quickly separated from each other.

According to the present invention, in the fluidized bed reactor, the cyclone may be any cyclone known to be suitable in the art, and the cyclone may comprise one or more group of cyclones and each group of cyclones may comprise one, two or three cyclones in series, thus, the solid catalysts entrained in the product streams can be thoroughly separated therefrom.

According to the present invention, in the fluidized bed reactor, the fast gas passage makes the fast gas-solid separation means in communication with the cyclone, and the fast gas passage is designed in such a size that the stream has a residence time therein as short as possible, e.g. the residence time is generally of not more than 5 s, preferably not more than 4 s, more preferably not more than 3 s.

According to the present invention, as to those lines provided with the fluidized bed reactor, i.e. the catalyst withdrawal line from the settling chamber in the lower portion of the separation zone and/or the dense phase zone of the reaction zone to the catalyst regeneration means, the catalyst return line from the catalyst regeneration means to the dense phase zone, and the catalyst recycle line from the lower portion of the separation zone to the dense phase zone, all these lines may be provided with suitable valves to adjust the flow-rates of the catalysts therein, and by adjusting the recycle flowrate of the catalyst and/or the return flowrate of the regenerated catalyst, the catalyst inventory in the dense phase zone and the average catalyst activity can be adjusted, so that the conversions of the materials in the dense phase zone and the riser can be adjusted accordingly.

According to the present invention, the reaction mixture out of the fluidized bed reactor can be introduced into the product process unit to be separated and/or purified to obtain the final product olefins such as ethylene and/or propylene, and the separation and/or purification may be carried out in any unit such as distillation column and absorption column known to be suitable in the art.

According to the present invention, the oxygenates to be converted may be those lower carbon alcohols and/or ethers usually used in the art, e.g., the oxygenates may be selected from the group consisting of methanol, ethanol, propanol, dimethyl ether, diethyl ether, dipropyl ether and mixture thereof, preferably methanol and/or dimethyl ether; and the lower olefins may be selected from the group consisting of ethylene, propylene, butylene and mixture thereof, preferably ethylene and/or propylene.

According to the present invention, the diluents added into the feed is intended to reduce the partial pressures of the feed and the produced product, and the diluent may be any suitable gas being inert during the reaction from oxygenates to olefins, e.g. it may be steam or nitrogen, preferably steam; herein, the diluent may be added at an amount of 5-80 mol %, preferably 10-60 mol %, more preferably 15-50 mol % on the basis of the feed mixture.

According to the present invention, the catalyst used for the reaction from oxygenates to olefins is generally the aluminosilicophosphate molecular sieves, e.g. the catalyst may be selected from the group consisting of SAPO-5, SAPO-11, SAPO-17, SAPO-41, SAPO-34 and SAPO-41, preferably SAPO-34.

According to the present invention, as to the reaction temperature used for the reaction of the oxygenates in the presence of SAPO catalyst, those skilled in the art can make choices depending on the specific oxygenates, generally, the reaction temperature used for the reaction from oxygenates to olefins may be in the range of 300-600°, preferably in the range of 400-550°.

According to the present invention, as to the reaction pressure used for the reaction of the oxygenates in the presence of SAPO catalyst, those skilled in the art can make choices depending on the specific oxygenates with consideration about the design and operation cost of the fluidized bed reactor, generally, the reaction pressure used for the reaction from oxygenates to olefins may be in the range of 0.05-1 MPa absolute, preferably in the range of 0.1-0.5 MPa absolute.

According to the present invention, as to the deactivation of the SAPO catalyst due to the carbon deposition thereon resulted from the reaction of the oxygenates, an oxygen comprising gas such as air, oxygen enriched air or pure oxygen, preferably air may be used to burn the carbon deposition off the catalyst surface to regenerate the catalyst, herein, in the catalyst regeneration means the temperature is generally in the range of 500-800° C., preferably in the range of 350-700° C., and the pressure is generally in the range of 0.05-1 MPa absolute, preferably in the range of 0.15-0.8 MPa absolute.

According to the present invention, the fluidized bed reactor comprises the dense phase zone and the riser in combination in the reaction zone, wherein most of the feed stream is converted in the dense phase zone and the remaining feed stream is further converted in the riser. Thus, provided that the targeted conversion of the feed stream being determined, the incorporation of the riser reduces the catalyst inventory in the dense phase zone. The catalyst inventory in the dense phase zone and the average catalyst activity may be further adjusted by the recycle and regeneration of the catalyst. Thus, the reaction degree of the feed stream can be further adjusted and the conversion of the feed stream can be optimized accordingly.

According to the present invention, the fluidized bed reactor comprises the fast gas-solid separation means and the cyclone in combination in the separation zone, wherein most of the catalyst is quickly separated by the fast gas-solid separation means and the remaining catalyst is further separated by the cyclone, and wherein the fast gas passage makes the fast gas-solid separation means in communication with the cyclone, thus, the separation time of the gas from the solid can be reduced as much as possible and the secondary reactions of the product olefins can be inhibited accordingly, so increasing the selectivity to the targeted product.

Thus, according to the present invention, the fluidized bed reactor comprises the dense phase zone and the riser in combination to control the reaction degree and optimize the conversion, and further comprises the fast gas-solid separation means and the cyclone in combination to quickly separate the gas from the solid and inhibit the secondary reactions, thus, ensuring the selectivity to the targeted product olefins.

Thus, the fluidized bed reactor according to the present invention can adjust and/or control the overall conversion and selectivity from oxygenates to olefins, so that to reach the best reaction effects and thereby to achieve the inventive purpose.

BRIEF DESCRIPTION OF THE DRAWINGS

In FIG. 1, a specific example of the fluidized bed reactor according to the present invention is shown, wherein the dense phase zone and the riser is connected transitionally by a truncated cone conduit, the fast gas-solid separation means is a vortex type fast gas-solid separation means, the cyclone is a two-staged cyclone comprising two cyclones in series, and a part of the deactivated catalyst is withdrawn from the settling chamber to the catalyst regeneration means to be regenerated therein.

In FIG. 1, the reference numerals are distributed as following: 1—feed inlet distributor; 2—dense phase zone; 3—internals; 4—riser; 5—vortex type fast gas-solid separation means; 6—leg of the vortex type fast gas-solid separation means; 7—fast gas passage; 8—cyclone; 9—leg of the cyclone; 10—gas collecting chamber; 11—reactor outlet; 12—product process unit; 13—stripping gas distributor; 14—settling chamber; 15—stripped mixture guiding line; 16—catalyst withdrawal line; 17—valve for adjusting the withdrawal flowrate of the deactivated catalyst; 18—catalyst regeneration means; 19—catalyst return line; 20—valve for adjusting the return flowrate of the regenerated catalyst; 21—catalyst recycle line; 22—valve for adjusting the recycle flowrate of the catalyst.

DETAILED DESCRIPTION OF THE INVENTION

The fluidized bed reactor as well as the process for producing olefins from oxygenates according to the present invention now is further illustrated in details with reference to the drawings.

Referring to FIG. 1, a feed stream comprising oxygenates such as methanol and/or dimethyl ether and a diluent such as steam is introduced into dense phase zone 2 in the lower portion of the fluidized bed reactor via feed inlet distributor 1, wherein the feed is reacted in the presence of a catalyst with a residence time e.g. of 4-10 s to be converted mostly to olefins, and at the same time a part of the catalyst is deactivated due to a carbon deposition thereon, the reaction heat is removed by internals 3 so that the reaction temperature is kept in a range e.g. of 400-550° and the reaction pressure is kept in the range of 0.1-0.5 MPa absolute, and the gas and solid backmixing is inhibited by internals 3 too;

A reaction mixture comprising lower olefins, unreacted feed and catalyst is directed from dense phase zone 2 upwardly into riser 4, wherein the unreacted feed is further converted almost completely in the presence of the catalyst with a residence time e.g. of 1-3 s, thus yielding a riser effluent primarily comprising lower olefins and catalyst;

The riser effluent is entering firstly into vortex type fast gas-solid separation means 5, wherein most of the catalyst is separated, then via fast gas passage 7 with a short residence time e.g. of not more than 3 s into cyclone 8, wherein the remaining catalyst is separated furthermore, and then into gas collecting chamber 10, and then exiting through reactor outlet 11, and finally is introduced into product process unit 12 to be separated to obtain final product olefins; and all the separated catalyst falls into settling chamber 14 in the lower portion of the separation zone via leg 6 of vortex type fast gas-solid separation means 5 and leg 9 of cyclone 8;

A part of the catalyst is recycled from settling chamber 14 back to dense phase zone 2 via catalyst recycle line 21, a part of the deactivated catalyst is withdrawn via catalyst withdrawal line 16 from settling chamber 14 to catalyst regeneration means 18 to be regenerated therein by burning off the deposited carbon at a temperature of 500-750° C. and a pressure of 0.1-0.5 MPa absolute, and then a part of the regenerated catalyst is returned from catalyst regeneration means 18 to dense phase zone 2 via catalyst return line 19; herein, by adjusting the recycle flowrate of the catalyst, the withdrawal flowrate of the deactivated catalyst and the return flowrate of the regenerated catalyst, the catalyst in dense phase zone 2 is with a better activity for the reaction; and Steam as stripping gas is introduced into settling chamber 14 via stripping gas distributor 13 to strip the catalyst, and the stripped gas mixture is passed to cyclone 8 via stripped mixture guiding line 15 at the upper side of settling chamber 14.

Now the present invention is further illustrated by the following example and comparative example, the example is not intended to limit the scope of the present invention.

EXAMPLES

Example 1

The fluidized bed reactor shown in FIG. 1 is used as the reactor, a mixture of methanol and steam is used as the feed, wherein the steam as diluent is of 30 mol % of the mixture, and the overall flowrate of the feed is of 67 kmol/h; catalyst is SAPO-34 at a load of 0.5 t; the reaction temperature is of 485 ▫ and the reaction pressure is of 0.2 MPa absolute; in the dense phase zone the superficial gas velocity is of 0.5 m/s and the residence time is of 5 s; in the riser the superficial gas velocity is of 8 m/s and the residence time is of 1.5 s; in the fast gas passage the residence time is of 1 s; steam is used as the stripping gas at a flowrate of 50 kg/h; from the settling chamber to the dense phase zone the recycle flowrate of the catalyst is of 3 t/h, from the settling chamber to the catalyst regeneration means the flowrate of the deactivated catalyst is of 0.5 t/h, in the catalyst regeneration means the regeneration temperature is of 650 ▫ and the regeneration pressure is of 0.22 MPa absolute, and the regenerated catalyst is returned to the dense phase zone at a flowrate of 0.5 t/h; at the reactor outlet a sample is taken to determine the conversion of methanol of 99.95 mol % and the overall selectivity to ethylene and propylene of 82.3 mol % respectively.

Comparative Example 1

Example 1 is repeated except that the reactor is a conventional bubbling fluidized bed reactor, wherein the reaction zone is the dense phase zone, the separation zone is a three-staged cyclone comprising three cyclones in series, the catalyst load is of 2 t, and in the dense phase zone the superficial gas velocity is of 0.3 m/s and the residence time is of 8 s; at the reactor outlet a sample is taken to determine the conversion of methanol of 99.65 mol % and the overall selectivity to ethylene and propylene of 78.3 mol % respectively.

As known from the results of example 1 and comparative example 1, compared with the conventional bubbling bed reactor, the fluidized bed reactor according to the present invention can reach a higher conversion of feed and a higher overall selectivity to ethylene and propylene with a significantly reduced catalyst inventory, thus, the fluidized bed reactor according to the present invention had made significant technical improvements already.

The invention claimed is:

1. A fluidized bed reactor, comprising:
a reaction zone located in a lower portion of the fluidized bed reactor and comprising a lower dense phase zone and an upper riser, wherein the lower dense phase zone and the upper riser are connected with each other transitionally;
a separation zone located in an upper portion of the fluidized bed reactor and comprising a settling chamber, a fast gas-solid separator, a cyclone and a gas collecting chamber, wherein the upper riser extends upwardly into the separation zone and an outlet of the upper riser is connected with an inlet of the fast gas-solid separator, an outlet of the fast gas-solid separator is connected with an inlet of the cyclone via a fast gas passage, an outlet of the cyclone is connected with the gas collecting chamber, and the gas collecting chamber is located below a reactor outlet and connected with the reactor outlet; and
a catalyst recycle line configured to recycle a catalyst from the settling chamber back to the lower dense phase zone, a catalyst withdrawal line configured to withdraw a deactivated catalyst from at least one of the settling chamber and the lower dense phase zone to a catalyst regenerator, and a catalyst return line configured to return a regenerated catalyst from the catalyst regenerator to the lower dense phase zone,
wherein the fluidized bed reactor is suitable for producing an olefin from an oxygenate,
the lower dense phase zone has a height to diameter ratio of from 0.5 to 10,
the upper riser has a height to diameter ratio of from 2 to 20,
a diameter ratio of the lower dense phase zone to the upper riser is from 2 to 10, and
the fast gas passage is configured such that a stream resides in the fast gas passage for not more than 5 seconds.

2. The fluidized bed reactor according to claim 1, wherein the lower dense phase zone comprises an inner portion configured to remove reaction heat and/or prevent backmixing of gas and solid.

3. The fluidized bed reactor according to claim 1, wherein the height to diameter ratio of the lower dense phase zone is from 0.6 to 8,
the height to diameter ratio of the upper riser is from 3 to 15, and
the diameter ratio of the lower dense phase zone to the upper riser is from 2.5 to 8.

4. The fluidized bed reactor according to claim 3, wherein the height to diameter ratio of the lower dense zone is from 0.8 to 5,
the height to diameter ratio of the upper rise is from 4 to 10, and
the diameter ratio of the lower dense phase zone to the upper riser is from 3 to 6.

5. The fluidized bed reactor according to claim 1, wherein the settling chamber is located in a lower portion of the separation zone such that a catalyst separated in the separation zone is collected in the settling chamber, and
the settling chamber comprises a stripping gas distributor in an inside of the settling chamber such that a stripping gas is introduced to strip the catalyst, and a stripped mixture guiding line at an upper side of the settling chamber such that the stripped mixture is transferred to the cyclone to be separated.

6. The fluidized bed reactor according to claim 1, wherein the fast gas-solid separator is selected from the group consisting of a vortex type fast gas-solid separator, an ejection type fast gas-solid separator, an inverse L type fast gas-solid separator, a T type fast gas-solid separator, a multi-tube type fast gas-solid separator, and a rotary arm type fast gas-solid separator.

7. The fluidized bed reactor according to claim 1,
wherein the cyclone comprises at least one group of cyclones, and
each group of cyclones comprises one, two or three cyclones in series.

8. The fluidized bed reactor according to claim 1,
wherein the fast gas passage is configured such that the stream resides in the fast gas passage for not more than 4 seconds.

9. The fluidized bed reactor according to claim 8,
wherein the fast gas passage is configured such that the stream resides in the fast gas passage for not more than 3 seconds.

10. A process for producing an olefin from an oxygenate with the fluidized bed reactor according to claim 1, the process comprising:
introducing a feed stream comprising an oxygenate and a diluent into the lower dense phase zone in the lower portion of the fluidized bed reactor via a feed inlet distributor, such that the feed stream is reacted in the presence of a catalyst and that a part of a feed is converted to a lower olefin and a part of the catalyst is deactivated due to carbon deposition thereon;
directing a reaction mixture comprising the lower olefin, unreacted feed and the catalyst from the lower dense phase zone upwardly into the upper riser, such that substantially all of the unreacted feed is further converted to the lower olefin in the presence of the catalyst and that a riser effluent primarily comprising the lower olefin and the catalyst is produced;
entering the riser effluent directly into the separation zone in the upper portion of the fluidized bed reactor, wherein the riser effluent is first entered into the fast gas-solid separator such that most of the catalyst is separated, entered into the cyclone via the fast gas passage such that remaining catalyst is separated, entered into the gas collecting chamber, and then exited through the reactor outlet, and all the separated catalyst falls into the settling chamber in the lower portion of the separation zone; and
recycling a part of the catalyst from the settling chamber back to the lower dense phase zone via the catalyst recycle line, withdrawing a part of the deactivated catalyst from at least one of the settling chamber and the lower dense phase zone to the catalyst regenerator via the catalyst withdrawal line such that the deactivated catalyst is regenerated in the catalyst regenerator, and then returning a part of the regenerated catalyst from the catalyst regenerator to the lower dense phase zone via the catalyst return line;
wherein, when passing the lower dense phase zone, the stream has a superficial gas velocity of from 0.1 to 2 m/s, and a residence time of from 0.5 to 20 seconds,
when passing the upper riser, the stream has a superficial gas velocity of from 2 to 20 m/s, and a residence time of from 0.3 to 5 seconds, and
when passing the fast gas passage, the stream has a residence time of not more than 5 seconds.

11. The process according to claim 10, further comprising at least one of:
removing reaction heat; and
preventing backmixing of gas and solid by the inner portion in the lower dense phase zone.

12. The process according to claim 10,
wherein, when passing the lower dense phase zone, the stream has a superficial gas velocity of from 0.2 to 1.5 m/s, and a residence time of from 1 to 15 seconds,
when passing the upper riser, the stream has a superficial gas velocity of from 4 to 18 m/s, and a residence time of from 0.4 to 4 seconds, and
when passing the fast gas passage, the stream has a residence time of not more than 4 seconds.

13. The process according to claim 12,
wherein, when passing the lower dense phase zone, the stream has a superficial gas velocity of from 0.3 to 1.2 m/s, and a residence time of from 2 to 10 seconds, and
when passing the upper riser, the stream has a superficial gas velocity of from 5 to 15 m/s, and a residence time of from 0.5 to 3 seconds.

14. The process according to claim 10, further comprising:
introducing a stripping gas via the stripping gas distributor into the settling chamber to strip the catalyst, wherein the stripping gas is nitrogen or steam; and
passing a stripped gas mixture to the cyclone via a stripped mixture guiding line at the upper side of the settling chamber.

15. The process according to claim 10,
wherein the catalyst is selected from the group consisting of SAPO-5, SAPO-11, SAPO-17, SAPO-41, SAPO-34 and SAPO-41.

16. The process according to claim 15,
wherein, in the fluidized bed reactor, the reaction temperature is from 300 to 600° C., and the reaction pressure is from 0.05 to 1 MPa absolute.

17. The process according to claim 16,
wherein, in the fluidized bed reactor, the reaction temperature is from 400 to 550° C., and the reaction pressure is from 0.1-0.5 MPa absolute.

18. The process according to claim 10,
wherein the oxygenate is selected from the group consisting of methanol, ethanol, propanol, dimethyl ether, diethyl ether, dipropyl ether and a mixture thereof,
the diluent is nitrogen or steam, and
the olefin is selected from the group consisting of ethylene, propylene, butylene and a mixture thereof.

19. The process according to claim 18,
wherein the oxygenate is at least one of methanol and dimethyl ether,
the diluent is nitrogen or steam, and
the olefin is at least one of ethylene and propylene.

20. The process according to claim 10, further comprising:
introducing the reaction mixture out of the fluidized bed reactor into a product process unit such that the reaction mixture is separated, purified, or separated and purified to obtain the olefin.

* * * * *